US00PP30106P2

(12) United States Plant Patent
Heimovaara

(10) Patent No.: US PP30,106 P2
(45) Date of Patent: Jan. 15, 2019

(54) ***CHRYSANTHEMUM* PLANT NAMED 'ZANMUPAINT'**

(50) Latin Name: ***Chrysanthemum* x *morifolium* Ramat.**
Varietal Denomination: Zanmupaint

(71) Applicant: Van Zanten Breeding BV, Aalsmeer (NL)

(72) Inventor: Sjoukje Heimovaara, Valkenburg (NL)

(73) Assignee: VAN ZANTEN BREEDING BV, Aalsmeer (NL)

( * ) Notice: Subject to any disclaimer, the term of this patent is extended or adjusted under 35 U.S.C. 154(b) by 0 days.

(21) Appl. No.: 15/732,812

(22) Filed: Jan. 4, 2018

(51) Int. Cl.
*A01H 5/02* (2018.01)

(52) U.S. Cl.
USPC ..... Plt./287
CPC ..... *A01H 5/02* (2013.01)

(58) Field of Classification Search
USPC ..... Plt./287, 292
CPC ..... A01H 5/02
See application file for complete search history.

*Primary Examiner* — Kent L Bell
(74) *Attorney, Agent, or Firm* — Steptoe & Johnson LLP

(57) ABSTRACT

A *chrysanthemum* plant named 'Zanmupaint' characterized by its medium sized blooms with purple ray florets and prolific branching; natural season flowering date September 25; blooming for a period of 5 weeks.

3 Drawing Sheets

Botanical designation: *Chrysanthemum* x *morifolium* Ramat.

Cultivar denomination: 'Zanmupaint'.

RELATED CULTIVARS

This new plant cultivar 'Zanmupaint' is of the botanical classification *Chrysanthemum* x *morifolium* Ramat.

BACKGROUND OF THE INVENTION

The present invention relates to a new and distinct cultivar of *chrysanthemum* plant, botanically known as *Chrysanthemum* x *morifolium* Ramat., commercially known as a garden mum, and hereinafter referred to by the cultivar denomination 'Zanmupaint'. 'Zanmupaint' is a product of a breeding and selection program for outdoor pot mums (garden mums) which had the objective of creating new cultivars with a double type inflorescence, a natural season flowering date around September 25, blooming for a period of 5 weeks. 'Zanmupaint' is a seedling resulting from a cross of the female parent 36928 with the male parent 36888. Plants of the new cultivar 'Zanmupaint' differ from plants of the female parent in the following characteristics. (1) Inflorescence size. And (2) Plant vigor. (1) Inflorescences of 'Zanmupaint' are larger than those of the female parent. (2) Plants of 'Zanmupaint' are more vigorous than those of the female parent. Plants of the new cultivar 'Zanmupaint' differ from plants of the male parent in inflorescence color; inflorescences of 'Zanmupaint' are purple while those of the male parent are pink.

The new and distinct cultivar was discovered and selected as a flowering plant by Sjoukje Heimovaara on a cultivated field in Rijsenhout, The Netherlands in September 2012. The first act of asexual production of 'Zanmupaint' was accomplished when vegetative cuttings from the initial selection were propagated further in a controlled environment in November 2012 at Rijsenhout, the Netherlands. In summer, about 6-8 days are needed to initiate roots in cuttings of the new cultivar, after another 5 days rooted plants are formed. The new cultivar has been found to retain its distinctive characteristics through successive asexual propagations.

BRIEF DESCRIPTION OF THE DRAWINGS

The present invention of a new and distinct variety of *chrysanthemum* (of about 16 weeks) is shown in the accompanying drawings, the color being as nearly true as possible with color photographs of this type.

DESCRIPTION OF THE INVENTION

Figure 1:
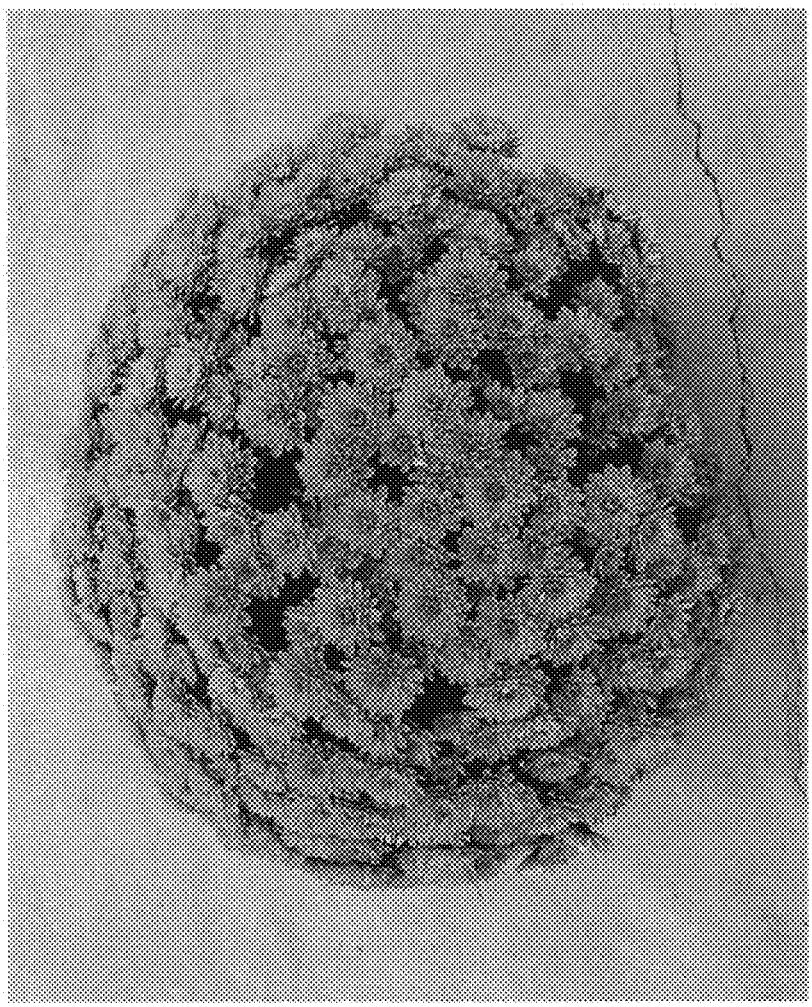
FIG. 1 shows a plant of the cultivar in full bloom.
Figure 2:
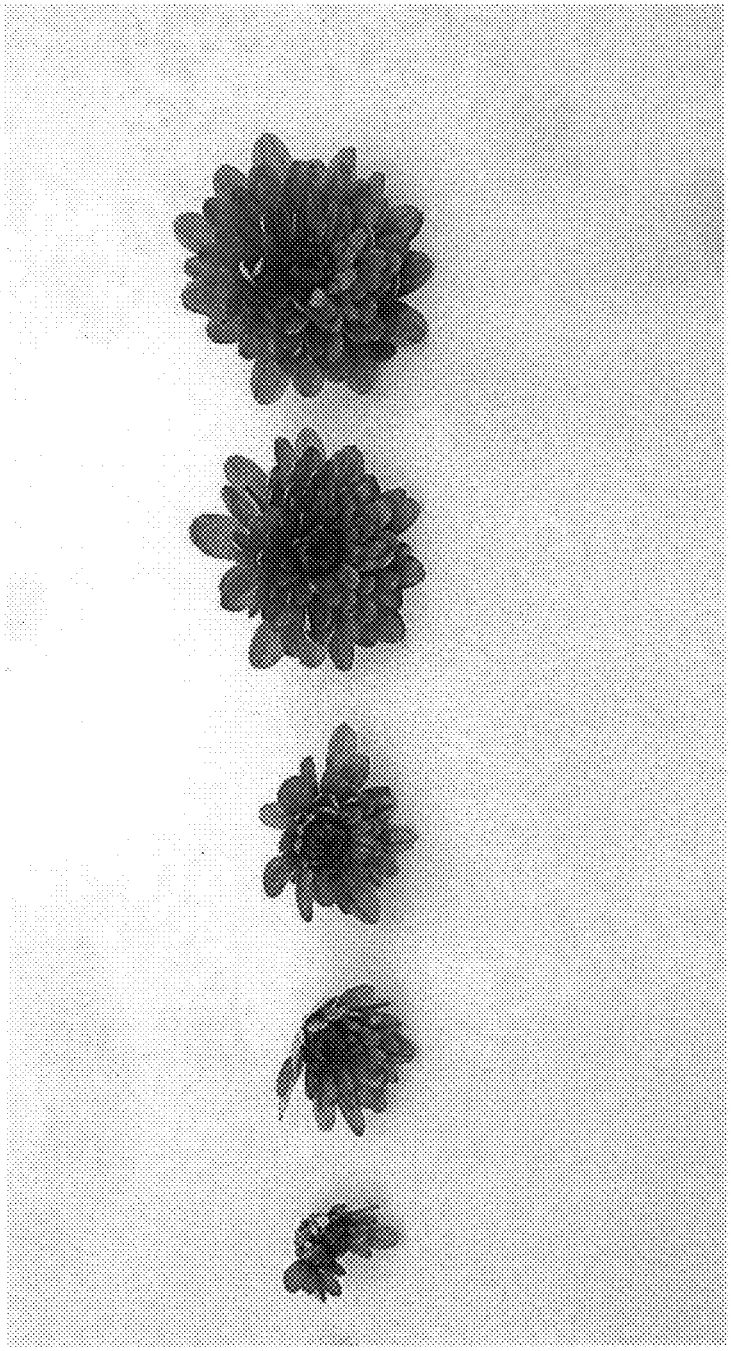
FIG. 2 shows the various stages of bloom of the new cultivar.
Figure 3:
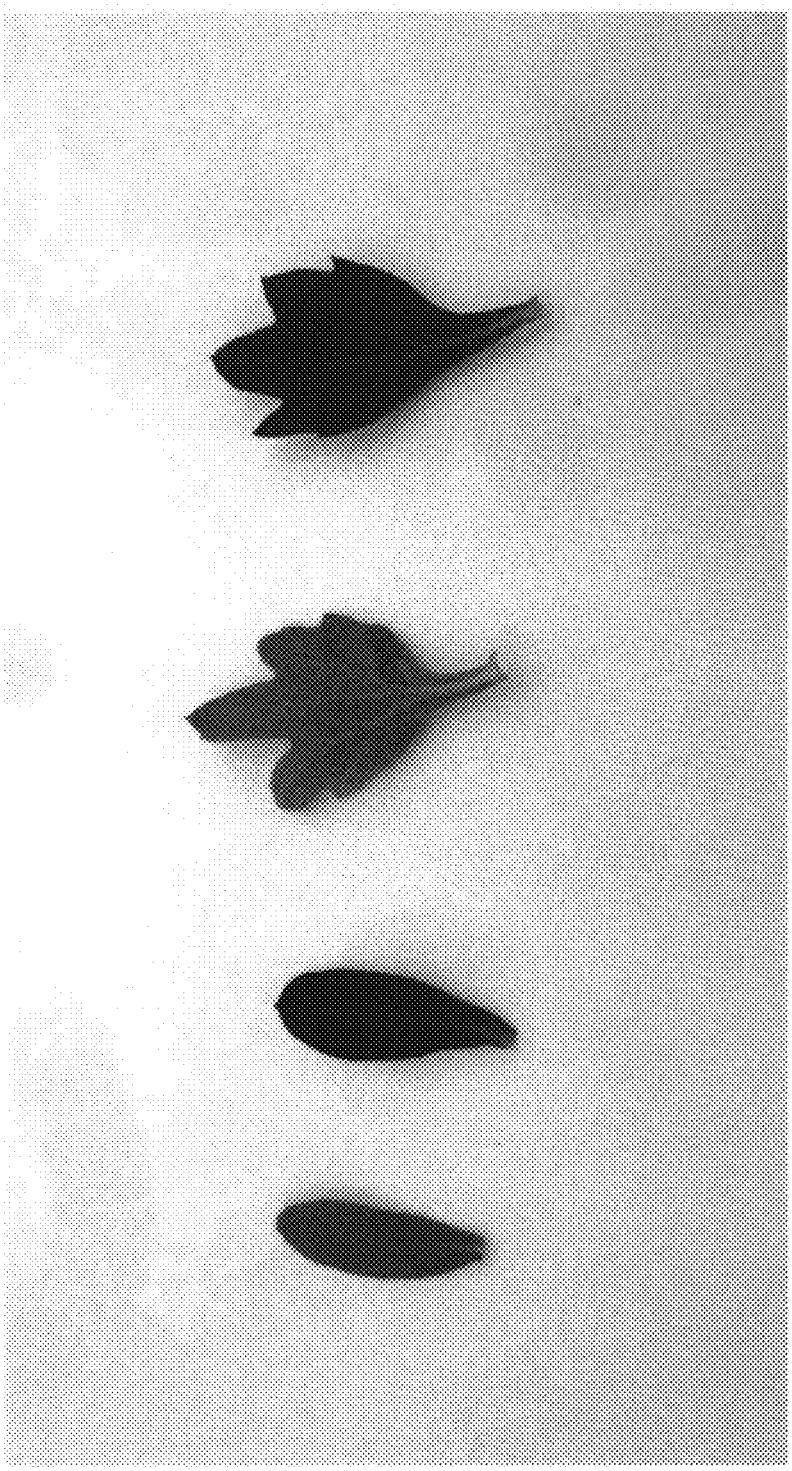
FIG. 3 shows the various stages of foliage of the new cultivar.

The observations and measurements were gathered from plants in the period of 14 to 19 weeks of age grown outdoor in Rijsenhout, the Netherlands, under natural day length and temperature and planted in week 23 in 2017, receiving drip irrigation. The natural blooming date of this crop was September 25 (week 39). The average height of the plants was 25 cm. No growth retardants were used. No tests were done on disease or insect resistance or susceptibility. No tests were done on cold or drought tolerance. This new variety produces medium sized blooms with purple ray florets blooming for a period of 5 weeks.

From the cultivars known to the inventor the most similar existing cultivar in comparison to 'Zanmupaint' is 'Venus' (U.S. Plant Pat. No. 14,378). When 'Venus' and 'Zanmupaint' are being compared the following differences are noticed: The differences of 'Venus' and 'Zanmupaint' are (1). Natural season blooming date. And (2). Inflorescence size. (1). Plants of 'Venus' flower earlier in the season than 'Zanmupaint'. (2). Inflorescences of 'Venus' are larger than those of 'Zanmupaint'.

The following is a description of the plant and characteristics that distinguish 'Zanmupaint' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, sixth edition (2015).

TABLE 1

Botanical Description of Chrysanthemum xmorifolium Ramat. 'Zanmupaint'

| | |
|---|---|
| **Bud** | |
| Size: | Small; cross-section 5 mm, height 3 mm |
| Shape: | Round |
| Texture: | Pubescent |
| Outside color: | Greyed-green 191A |
| **Phyllaries** | |
| Number: | 24, arranged in 3 rows |
| Shape: | Elliptic |
| Apex: | Acute |
| Base: | Truncate |
| Margin: | Entire |
| Color: | Upper side: Green 139B<br>Lower side: Green N138D |
| Length and width: | 5-6 mm; 1.5 mm |
| Texture: | Pubescent |
| **Inflorescences** | |
| Type: | Double |
| Height: | 2 cm |
| Diameter: | 4-4.5 cm |
| Peduncle length: | 7 cm |
| Peduncle color: | Green 139C |
| Peduncle diameter: | 0.8 mm |
| Peduncle texture: | Pubescent |
| Number per branch: | About. 8-9 inflorescences |
| Duration of flowering: | 5 weeks |
| Seeds: | Produced in small quantities, ovate, Greyed-brown 199A, length 1.5 mm, diameter 0.5 mm; texture: rough with ribs |
| Fragrance: | Faint chrysanthemum odor |
| **Color inflorescences** | |
| Center of inflorescence: | Immature stage: Red-purple 71A; Mature stage: Red-purple 71B |
| Color of upper side of ray florets: | Purple N78B |
| Color of lower side of ray florets: | Greyed-purple 186 B to 186C |
| Tonality from distance: | A garden mum with purple blooms and a dark center |
| Color of ray florets after aging of the plant: | Greyed-Purple 186D |
| **Ray florets** | |
| Number of types: | Two |
| Type: | Ligulate, occasionally spatulate |
| Rows: | About 15 |
| Texture: | Upper and lower side smooth |
| Number: | 220 to 240 |
| Shape: | Elliptic |
| Apex: | Dcntate. |
| Base: | Acute |
| Cross-section: | Flat |
| Longitudinal axis: | Straight |
| Length of corolla tube: | 2-6 mm |
| Diameter corolla tube: | 1 mm |
| Ray floret margin: | Entire |

TABLE 1-continued

Botanical Description of Chrysanthemum xmorifolium Ramat. 'Zanmupaint'

| | |
|---|---|
| Ray floret length: | 1-3 cm |
| Ray floret width: | 2-8 mm |
| Ratio length/width: | Medium |
| Disc florets | Absent |
| **Receptacle** | |
| Color: | Yellow-green 145D |
| Shape: | Domed raised |
| Height: | 4 mm |
| Diameter: | 7 mm |
| **Reproductive Organs** | |
| Androecium: | Absent |
| Pollen: | Lacking |
| Gynoecium: | Present in ray florets |
| Style color: | Yellow-green 154C |
| Style length: | 4 mm |
| Stigma color: | Yellow 7A |
| Stigma width: | 1 mm |
| Ovary: | Ellelosed in calyx |
| Ovary color: | Yellow-green 149D |
| **Plant** | |
| Type: | Bushy |
| Growth habit: | Spherical shape |
| Growth rate: | Medium |
| Height: | 25 cm |
| Width: | 45 cm |
| Stem color: | Greyed-brown 199A |
| Stem strength: | Not strong |
| Stem brittleness: | Brittle |
| Stem anthocyanin coloration: | Absent |
| Internode length: | 1.5 -2 cm |
| Length of lateral branch: | From top to bottom 16-17 cm |
| Lateral branch color: | Green 139 C |
| Lateral branch, attachment: | Weak |
| Lateral branch diameter: | 2 mm |
| Lateral branch, texture: | Pubescent with ribs |
| Branching (average number of lateral branches): | Medium with 8-9 breaks after pinching |
| Natural season blooming date: | September 25 (week 39) in Rijsenhout, the Netherlands |
| Roots - habits: | Fine, freely branching |
| Roots - color: | White 155A |
| **Foliage** | |
| Glossiness: | Leaf upper side: weak<br>Leaf lower side: very weak |
| Leaf color: | Upper side: Green 138A<br>Lower side: Green NN137D |
| Color midvein: | Upper side: Yellow-green 144B<br>Lower side: Yellow-green 144C |
| Size: | Small; length 2.5-5.5 cm, width 0.7-2.5 cm |
| Quantity (number per lateral branches): | ca. 30 |
| Shape: | Elliptic to widely elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |

TABLE 1-continued

| Botanical Description of Chrysanthemum xmorifolium Ramat. 'Zanmupaint' | |
|---|---|
| Shape of base: | Attenuate to truncate |
| Apex: | Mucronulate |
| Petiole strength: | Weak |
| Petiole attitude: | Moderately upwards |
| Petiole length: | 0.2-1 cm |
| Petiole diameter: | 0.2-2.5 mm |
| Petiole color: | Yellow-green 147D |
| Stipules: | Occasionally present at leaves from lower part of branches |

TABLE 2

| Differences with the comparison variety, when grown under identical conditions | | |
|---|---|---|
| | 'Zanmupaint' | 'Venus' |
| Natural season blooming date | Week 39 | Week 35 |
| Inflorescence size | 4-4.5 cm | 5-5.5 cm |

I claim:

1. A new and distinct *chrysanthemum* plant named 'Zanmupaint' as described and illustrated.

* * * * *